US00PP30582P2

(12) United States Plant Patent
Van Swieten

(10) Patent No.: US PP30,582 P2
(45) Date of Patent: Jun. 18, 2019

(54) ***PHALAENOPSIS* ORCHID PLANT NAMED 'PHALCUVAK'**

(50) Latin Name: ***Phalaenopsis* hybrid**
Varietal Denomination: PHALCUVAK

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/998,229

(22) Filed: Jul. 20, 2018

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALCUVAK', particularly characterized by having greenish-yellow flowers with red-purple lips, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALCUVAK'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALCUVAK'.

The new *Phalaenopsis* plant is a product of a planned breeding program conducted by the inventor in Bleiswijk, The Netherlands. The objective of this breeding program was to create a new *Phalaenopsis* plant with numerous attractive and greenish-yellow flowers with red-purple lips, suitable for potted plant production.

The new *Phalaenopsis* plant 'PHALCUVAK' is a result of cross-pollination made by the inventor in July 2002 in Bleiswijk, The Netherlands of the proprietary female, or seed parent, *Phalaenopsis* hybrid '20401-06' (unpatented) with the proprietary male, or pollen parent, *Phalaenopsis* hybrid '01-1350' (unpatented).

The new *Phalaenopsis* was selected by the inventor as a single plant within the progeny of the stated cross-pollination in a controlled greenhouse in Bleiswijk, The Netherlands in June 2006. Asexual reproduction of the new *Phalaenopsis* plant by meristem tissue culture since 2011 in Bleiswijk, The Netherlands, has demonstrated that the new variety reproduces true to type with all of the characteristics, as herein described, firmly fixed and retained through successive generations.

Plant Breeder's Rights for this variety have not been applied for to date. 'PHALCUVAK' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALCUVAK' as a new and distinct variety of *Phalaenopsis* plant.

1) Greenish-yellow flowers with red-purple lips;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in June 2018. Colors in the photographs may differ from the color values cited in the detailed botanical description, which accurately describe the actual colors of the new variety.

DESCRIPTION OF THE NEW VARIETY

Figure 1:
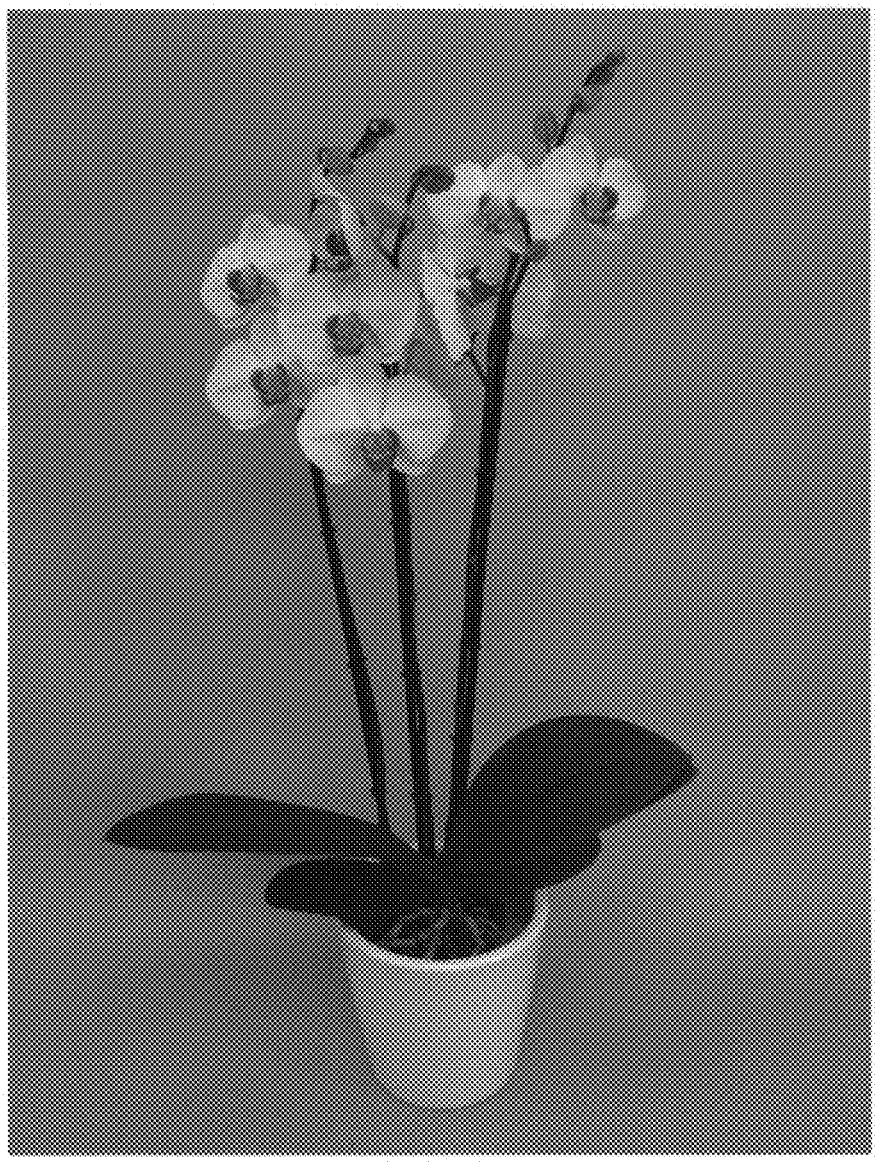
FIG. 1 shows the overall plant habit, including blooms, buds and foliage of 'PHALCUVAK'.
Figure 2:
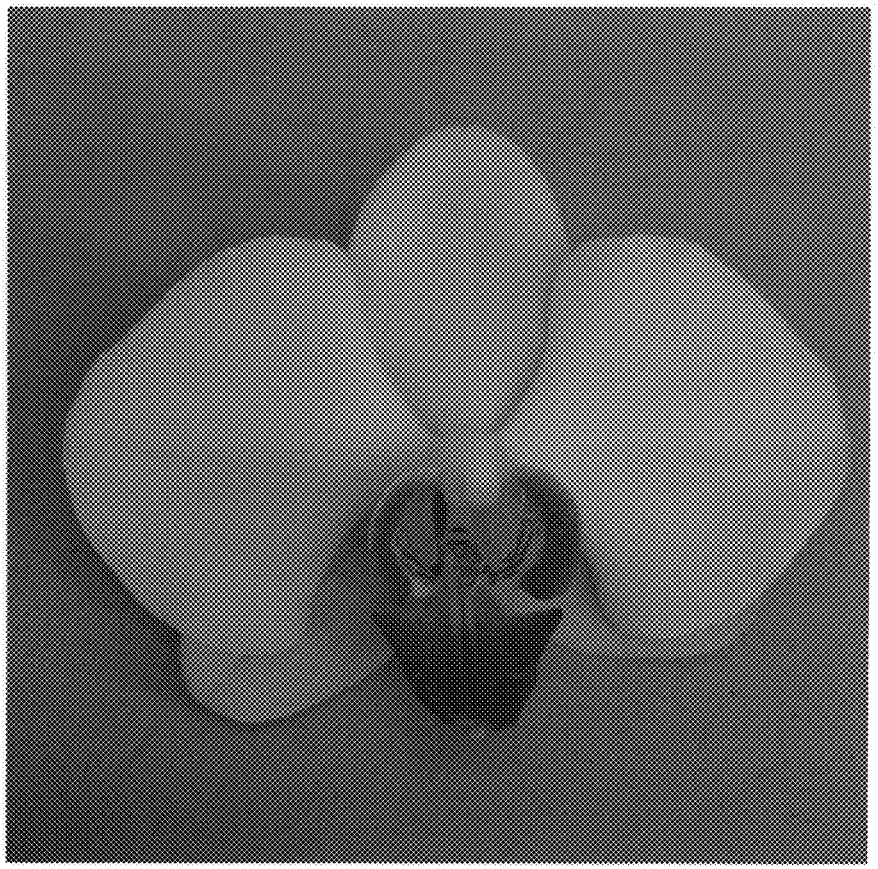
FIG. 2 shows a close-up of a flower of 'PHALCUVAK'.
Figure 3:
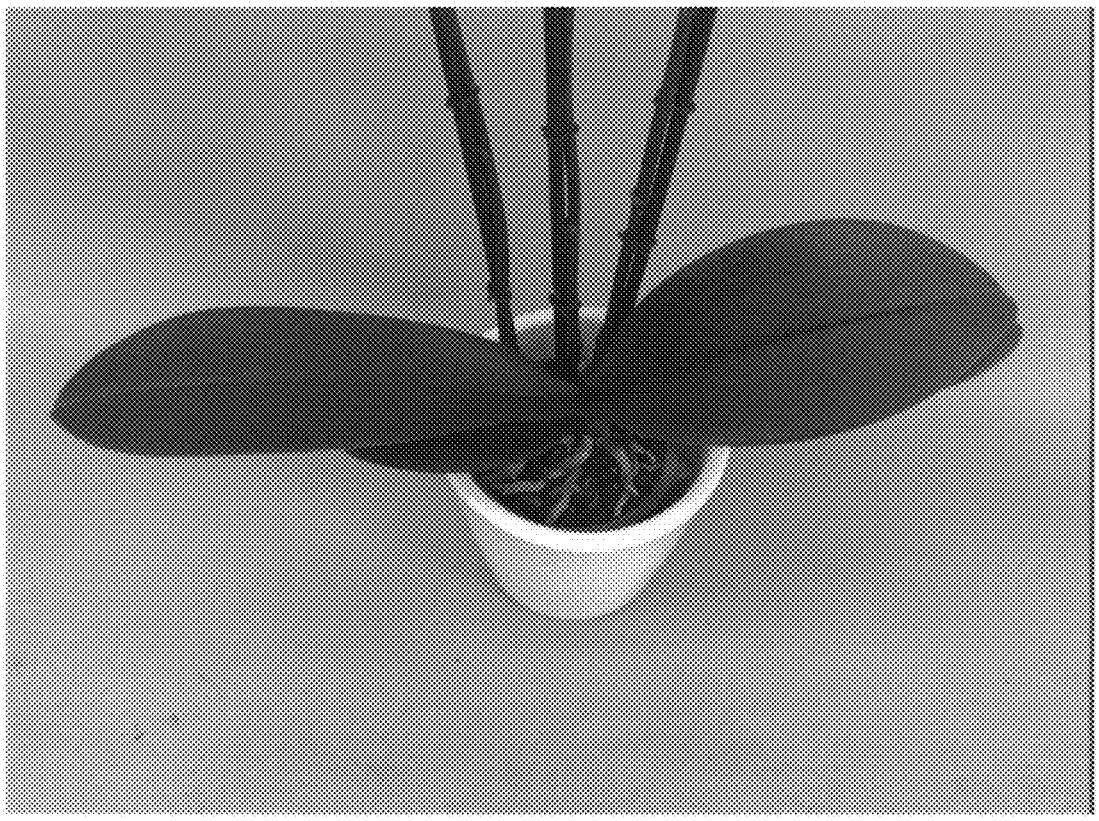
FIG. 3 shows an overhead view of the leaves of 'PHALCUVAK'.

The following detailed description sets forth the distinctive characteristics of 'PHALCUVAK'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in June 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50-weeks in a 12 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALCUVAK'.

Parentage:

*Female parent*.—*Phalaenopsis* cultivar '20401-06' (unpatented).

*Male parent*.—*Phalaenopsis* cultivar '01-1350' (unpatented).

Propagation:

*Type*.—Meristem tissue culture.

Roots:

*Root description*.—Greyed-green colored roots (RHS 190B/C) with branching lateral roots having light yellow-green (RHS 145D) colored root tips.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Upright to slightly pendant with raceme to panicle inflorescence.

*Height (from soil level to top of inflorescence)*.—Approximately 50.0 cm to 55.0 cm.

*Width (measured from leaf tips)*.—About 32.0 cm to 34.0 cm.

*Vigor*.—Moderate.

Leaves:

*Mature leaves*.—Quantity per plant: 9 to 11 leaves are produced before flowering. Length (fully expanded): 18.0 cm to 22.0 cm. Width: 7.5 cm to 8.5 cm. Shape: Oblong. Base shape: Moderately elongated. Apex: Obtuse unequal. Leaf blade angle with the petiole (measured from the horizontal position): Between 20 degrees and 40 degrees. Leaf margin: Entire. Color: Upper surface: RHS 146A. Lower surface: RHS 146B. Texture (upper surface): Rough. Thickness: 2.2 mm to 2.5 mm. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—6 to 12.

*Length*.—50.0 cm to 55.0 cm.

*Diameter*.—5.0 mm to 5.3 mm.

*Strength*.—Moderate.

*Aspect*.—Upright.

*Texture*.—Smooth.

*Color*.—Mix of green (RHS 146B) and brown (RHS N199A).

*Internode length*.—4.0 cm to 6.0 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 190.0 mm to 220.0 mm.

*Flowering time*.—First flowers can be expected 10 to 11 months after planting in a 12 cm (diameter) pot.

*Flower*.—Height: 67.0 mm to 72.0 mm. Diameter: 82.0 mm to 87.0 mm. Depth of lip: 25.0 mm to 27.0 mm.

*Flower longevity*.—On the plant: 9 to 15 weeks.

*Fragrance*.—Absent.

*Flower bud*.—Average size: Medium. Length: 22.0 mm to 24.0 mm. Width: 18.0 mm to 20.0 mm. Shape: Egg shaped. Color: Yellowish-green (RHS N144D).

*Petals*.—Arrangement: Open/free. Shape: Semi-circular. Apex: Rounded asymmetric. Margin: Slightly undulated. Length (from base to tip): 38.0 mm to 40.0 mm. Width: 49.0 mm to 51.0 mm. Color (when fully opened): Upper surface: Basic color: Light yellow-green (RHS 145D). Over color: Absent. Lower surface: Basic color: Light yellow-green (RHS 145D). Over color: Light yellow-green (RHS 145C).

*Dorsal sepal*.—Shape: Elliptic. Apex: Rounded to slightly emarginated. Margin: Entire. Length (from base to tip): 39.0 mm to 41.0 mm. Width: 29.0 mm to 31.0 mm. Color (when fully opened): Upper surface: Basic color: Light yellow-green (RHS 145D). Over color: Light yellow-green (RHS 145C). Lower surface: Basic color: Light yellow-green (RHS 145C). Over color: Diluting green (RHS N144A).

*Lateral sepals*.—Shape: Ovate. Apex: Obtuse asymmetric. Margin: Entire. Length (from base to tip): 39.0 mm to 41.0 mm. Width: 24.0 mm to 26.0 mm. Color (when fully opened): Upper surface: Basic color: Light yellow-green (RHS 145D). Over color: Light yellow-green (RHS 145C) and purplish-red middle stripe (RHS 185C) at the base. Lower surface: Basic color: Light yellow-green (RHS 145C). Over color: Middle vein green (RHS N144A).

*Labellum (lip)*.—Whiskers: Present. Length of whiskers: 17.0 mm to 19.0 mm. Color of whiskers: Dark red (RHS 59A) with light greenish-yellow tips (RHS 4C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 19.0 mm to 21.0 mm. Width: 14.0 mm to 16.0 mm. Color: Light greenish-yellow (RHS 4B and 4C) at the base with red stripes (RHS 178A); white (RHS NN155C) toward one side; red (RHS 180A) toward other side; purple-red (RHS 72A and 72B) toward the tip.

*Apical lobe*.—Shape: Triangular. Margin: Entire. Length: 21.0 mm to 23.0 mm. Width: 19.0 mm to 21.0 mm. Color: Slightly light greenish-yellow (RHS 4C) at the base; slightly dark red wings (RHS 59A); purplish-red (RHS 71A) toward the whiskers.

*Callus*.—Average size: Medium. Height: 6.0 mm to 7.0 mm. Length: 5.0 mm to 6.0 mm. Width: 4.0 mm to 5.0 mm. Color: Light greenish-yellow (RHS 4A and 4C) dotted (RHS 178B).

Reproductive organs:

*Column*.—Length: 8.0 mm to 10.0 mm. Diameter: 5.0 mm to 5.4 mm. Color: White (RHS NN155C).

*Pollinia*.—Quantity: 2. Diameter: 0.9 mm to 1.1 mm. Color: Orange (RHS 24A).

*Ovary*.—Length: 11.0 mm to 13.0 mm. Diameter: 2.3 mm to 2.6 mm. Color: Light green (RHS 145C).

*Pedicel*.—Length: 36.0 mm to 38.0 mm. Diameter: 2.8 mm to 3.3 mm. Color: Mix of light yellow-green (RHS 145B) and purple (RHS N77A) at the base; light yellow-green (RHS 145C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALCUVAK', cultivar '20401-06', is no longer in existence, so a meaningful comparison cannot be made.

'PHALCUVAK' differs from male parent plant '01-1350' (unpatented) in that 'PHALCUVAK' has light yellow-green flowers, whereas '01-1350' has dark purplish-red flowers. Additionally, 'PHALCUVAK' has larger flowers, longer whiskers and wider petals than '01-1350'.

'PHALCUVAK' is most similar to the commercial *Phalaenopsis* plants named 'PHALFYQDHA' (U.S. Plant Pat. No. 27,456) and 'PHALCISYP' (U.S. Plant Pat. No. 28,779). 'PHALCUVAK' differs from the commercial variety 'PHALFYQDHA' in that 'PHALCUVAK' has light yellow-green (RHS 145D) flowers with an even pattern and a rounded to slightly emarginated dorsal sepal apex, whereas 'PHALFYQDHA' has yellow (RHS 4D) flowers with a small white center and an obtuse symmetric dorsal sepal apex. Additionally, 'PHALCUVAK' has wider petals than 'PHALFYQDHA'.

'PHALCUVAK' differs from the commercial variety 'PHALCISYP' in that 'PHALCUVAK' has an even flower pattern and a slightly undulated petal margin, whereas 'PHALCISYP' has a center flower pattern and an entire petal margin. Additionally, 'PHALCUVAK' has smaller flowers, longer whiskers, and narrower petals than 'PHALCISYP'.

I claim:

1. A new and distinct variety of *Phalaenopsis* plant named 'PHALCUVAK', substantially as described and illustrated herein.

* * * * *